United States Patent [19]

Isomura et al.

[11] Patent Number: 5,442,110

[45] Date of Patent: Aug. 15, 1995

[54] HYDROXAMIC ACID DERIVATIVE

[75] Inventors: Yasuo Isomura; Seijiro Akamatsu; Toru Yoden; Masafumi Kudou; Akira Suga, all of Ibaraki, Japan

[73] Assignee: Yamanouchi Pharmaceutical Co., Ltd., Tokyo, Japan

[21] Appl. No.: 211,934

[22] PCT Filed: Nov. 2, 1994

[86] PCT No.: PCT/JP92/01421

§ 371 Date: Apr. 20, 1994

§ 102(e) Date: Apr. 20, 1994

[87] PCT Pub. No.: WO93/09090

PCT Pub. Date: May 13, 1993

[30] Foreign Application Priority Data

Nov. 6, 1991 [JP] Japan .................. 3-318467

[51] Int. Cl.$^6$ .......................... C07C 259/06
[52] U.S. Cl. ...................... 562/621; 562/623
[58] Field of Search .................. 562/621, 623

[56] References Cited

PUBLICATIONS

Matsuda, et al, Bunseki Kagaku (1986) 35(3) 151–156 *Abstract*.

Primary Examiner—José G. Dees
Assistant Examiner—Joseph M. Conrad, III
Attorney, Agent, or Firm—Burgess, Ryan & Wayne

[57] ABSTRACT

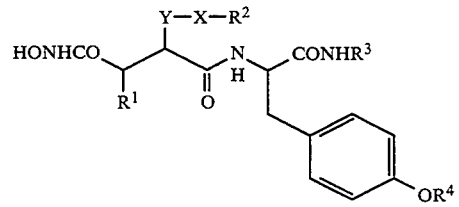

A compound represented by general formula (I), a pharmaceutical composition containing same, a process for the production thereof, and an intermediate therefor. In formula (I) $R^1$ represents lower alkyl which may be substituted by a substituent selected from the group consisting of mercapto, lower alkylthio, arylthio and lower acylthio; $R^2$, $R^3$ and $R^4$ may be the same or different from one another and each represents lower alkyl; X represents oxygen or sulfur; and Y represents a single bond or lower alkylene. The compound (I) has a matrix metalloprotease inhibitory activity and is useful for preventing and treating diseases caused by the progress of connective tissue breakage.

7 Claims, No Drawings

5,442,110

HYDROXAMIC ACID DERIVATIVE

This application is a 371 of PCT/JP92/01421 filed Nov. 2nd, 1992.

TECHNICAL FIELD

This invention relates to a hydroxamic acid derivative which is useful as a therapeutic agent for the prevention and treatment of diseases caused by the progress of connective tissue destruction, a process for the production thereof and a pharmaceutical composition containing the same.

BACKGROUND ART

It is considered that collagen and proteoglycan as the principal components of mammalian connective tissues are degraded by a matrix metalloprotease (MMP) in a specific fashion and then by other proteolytic enzymes. Examples of known matrix metalloproteases include collagenase (MMP1), gelatinase (MMP2), proteoglycanase (MMP3) and the like. It is also considered that these matrix metalloproteases, together with a tissue inhibitor of metalloprotease (TIMP) as their biological inhibiting factor and α2-macroglobulin, are taking a great role in controlling metabolism of connective tissues, and that the progress of connective tissue destruction occurs when collagen and proteoglycan are degraded by the matrix metalloprotease formed in an excess amount due to the unbalanced levels of the matrix metalloprotease and the biological inhibiting factor.

In consequence, a matrix metalloprotease inhibitor which represses tissue destruction through its activity to inhibit the aforementioned degradation by matrix metalloproteases will be useful for the prevention and treatment of diseases which are believed to be caused by the progress of connective tissue destruction, such as arthritis (e.g., chronic articular rheumatism and osteoarthritis), periodontal disease, corneal ulcer, epidermolysis bullosa, neoplastic infiltration, abnormal bone resorption and the like.

A number of studies have been conducted on the development of pharmaceutical compounds capable of repressing degradation of collagen through their activity to inhibit enzyme activity of collagenase, and such compounds so far reported are roughly divided into certain phosphoric acid derivatives and hydroxamic acid derivatives.

Especially, with regard to a hydroxamic acid derivative which relates to the compound of the present invention, Japanese Patent Application Toppyo Hei. 4-502008 (international publication WO90/05719) discloses a compound represented by the following general formula as a hydroxamic acid-based collagenase inhibitor.

(In the above formula,

R$^1$ represents C$_1$-C$_6$ alkyl, phenyl, thiophenyl, substituted phenyl, phenyl (C$_1$-C$_6$) alkyl, heterocyclyl, (C$_1$-C$_6$) alkylcarbonyl, phenacyl or substituted phenacyl or, when n=0, R$^1$ is —SR$^x$ where R$^x$ represents the following group, R$^2$ represents a hydrogen atom:, C$_1$-C$_6$ alkyl, C$_1$-C$_6$ alkenyl, phenyl (C$_1$-C$_6$) alkyl, cycloalkyl (C$_1$-C$_6$) alkyl or cycloalkenyl (C$_1$-C$_6$) alkyl, R$^3$ represents an amino acid side chain or C$_1$-C$_6$ alkyl, benzyl, (C$_1$-C$_6$ alkoxy) benzyl, benzyloxy (C$_1$-C$_6$ alkyl) or benzyloxybenzyl, R$^4$ represents a hydrogen atom or C$_1$-C$_6$ alkyl, R$^5$ represents a hydrogen atom or methyl, n is an integer of 0, 1 or 2, and A represents a C$_1$-C$_6$ hydrocarbon chain, optionally substituted by one or more C$_1$-C$_6$ alkyl, phenyl or substituted phenyl.)

However, when pharmacological, toxicological or physicochemical properties of collagenase inhibitors so far available are taken into consideration, a matrix metalloprotease inhibitor requires further improvement in terms of stable or enhanced in vivo pharmacological activity, extension of its effective range on other matrix metalloproteases, reduction of toxicity, improvement of solubility and the like.

DISCLOSURE OF THE INVENTION

The inventors of the present invention have found that a novel hydroxamic acid derivative whose chemical structure is different from those of the known collagenase inhibitors has an excellent collagenase inhibitory activity and can be used as a therapeutic agent for the prevention and treatment of diseases caused by the progress of connective tissue destruction, and have accomplished the present invention on the basis of these findings.

Accordingly, the present invention relates to a compound represented by the following general formula (I):

(each symbol in this formula means as follows;

R$^1$: a lower alkyl group which may be substituted by a substituent group selected from the class consisting of a mercapto group, a lower alkylthio group, an arylthio group and a lower acylthio group, R$^2$, R$^3$ and R$^4$: the same or different from one another and each represents a lower alkyl group, X: an oxygen atom or a sulfur atom, Y: a single bond or a lower alkylene group), a pharmaceutically acceptable salt thereof, a pharmaceutically acceptable hydrate thereof, a pharmaceutically acceptable solvate thereof or a stereoisomer thereof.

The present invention also relates to a process for the production of the aforementioned compound (I) and the like and to a pharmaceuticalscomposition containing the same.

It also relates to an intermediate represented by the following general formula (II):

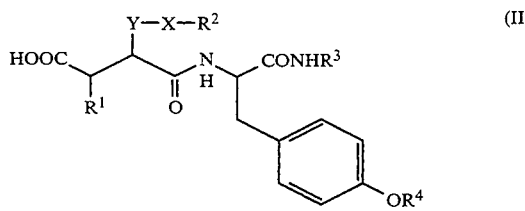

(in this formula, $R^1$, $R^2$, $R^3$, $R^4$, X and Y have the same respective meanings as described above) which is useful as a production intermediate of the aforementioned compound (I), a salt thereof or a stereoisomer thereof.

The compound (I) of the present invention has a characteristic chemical structure in which a position corresponding to $R^2$ of the compound disclosed in the aforementioned Japanese Patent Application Toppyo Hei. 4-502008 has a —Y—X—$R^2$ form and it has an ether or thioether structure. Also, chemical structure of the compound of the present invention is different from that of the compound illustratively disclosed in the just described patent, because Examples in this patent application discloses only a compound whose $R^3$ is a benzyl group, while a group of the compound of the present invention corresponding to the $R^3$ is a benzyl group which is always substituted by a lower alkoxy group.

In addition, the aforementioned patent application discloses only in vitro collagenase activity, but nothing about its in vivo effects.

The following describes the compound of the present invention in detail.

In the definition of the general formulae of the present specification, the term "lower" means a straight or branched carbon chain having 1 to 6 carbon atoms.

In consequence, the term "lower alkyl group" means a straight or branched-chain $C_{1-6}$ alkyl group, with its illustrative examples including a methyl group, an ethyl group, a propyl group, an isopropyl group, a butyl group, an isobutyl group, a sec-butyl group, a tert-butyl group, a pentyl group, an isopentyl group, a hexyl group, an isohexyl group and the like.

Especially, a straight or branched-chain $C_{1-4}$ alkyl group, particularly a methyl group, is preferable as the lower alkyl group, or the lower alkyl group which may be substituted by a substituent, of $R^1$, $R^3$ and $R^4$. As the lower alkyl group of $R^2$, a straight or branched-chain $C_{1-4}$ alkyl group, particularly a propyl group, is preferred.

Illustrative examples of the "lower alkylthio group" as a substituent of the $R^1$ lower alkyl group include straight or branched-chain $C_{1-6}$ alkylthio groups such as a methylthio group, an ethylthio group, a propylthio group, an isopropylthio group, a butylthio group, an isobutylthio group, a sec-butylthio group, a tert-butylthio group, a pentylthio group, a hexylthio group and the like, of which $C_{1-4}$ alkylthio groups such as a methylthio group, an isopropylthio group and the like are particularly preferred.

Illustrative examples of the substituent "arylthio group" include $C_{6-10}$ arylthio groups such as a phenylthio group, a tolylthio group, a methoxyphenylthio group, a naphthylthio group and the like, of which a phenylthio group is particularly preferred.

Illustrative examples of the substituent "lower acylthio group" include straight or branched-chain $C_{1-6}$ acylthio groups such as a formylthio group, an acetylthio group, a propionylthio group, a butylylthio group, an isobutylylthio group, a valerylthio group, a hexanoylthio group and the like, of which an acetylthio group is particularly preferred.

Illustrative examples of the "lower alkylene group" represented by Y include straight or branched-chain $C_{1-6}$ alkylene groups such as a methylene group, an ethylene group, a methylmethylene group, a trimethylene group, a propylene group, a tetramethylene group, a pentamethylene group, a hexamethylene group and the like, of which $C_{1-3}$ alkylene groups such as a methylene group are particularly preferred.

The compounds (I) and (II) of the present invention form salts with bases. Pharmaceutically acceptable salts of the compound (I) and salts of the compound (II) are also included in the present invention, and illustrative examples of such salts include salts with alkali metals such as sodium, potassium and the like, salts with alkaline earth metals such as magnesium, calcium and the like, salts with aluminum, salts with organic bases such as methylamine, ethylamine, dimethylamine, diethylamine, trimethylamine, triethylamine, diethanolamine, cyclohexylamine, lysine, ornithine and the like and salts with ammonium.

Each of the compounds (I) and (II) of the present invention has at least 3 asymmetric carbon atoms in its molecule, and their presence results in the formation of at least 8 stereoisomers. All stereoisomers of the compounds (I) and (II), such as opticalantipodes, diastereomers and the like and their mixtures (racemic compounds), are included in the present invention, and it should be understood therefore that the term "stereoisomer" used herein and in the claim also includes these racemic compounds.

The present invention also includes pharmaceutically acceptable hydrates, pharmaceutically acceptable solvates and crystalline polymorphism of the compound (I).

Preferred examples of the compound (I) of the present invention are compounds whose —Y—X—$R^2$ is a propoxymethyl group or a propylthio group, especially whose —Y—X—$R^2$ is a propoxymethyl group or a propylthio group and $R^1$ is a lower alkyl group or a lower alkylthiomethyl group.

Typical examples of the compound of the present invention are as follows.

(1) (N$^\alpha$-[3-(N-hydroxycarbamoyl)-4-methylthio-2-propoxymethyl)butylyl]-N,O-dimethyltyrosine amide, a pharmaceutically acceptable salt thereof and a stereoisomer thereof (2) (N$^\alpha$-[3-(N-hydroxycarbamoyl)-4-isopropylthio-2-propoxymethyl)butylyl]-N,O-dimethyltyrosine amide, a pharmaceutically acceptable salt thereof and a stereoisomer thereof (3) (N$^\alpha$-[3-(N-hydroxycarbamoyl)-2-propylthio)-butylyl]-N,O-dimethyltyrosine amide, a pharmaceutically acceptable salt thereof and a stereoisomer thereof.

The compound of the present invention represented by the general formula (I) can be produced by various synthesis methods making use of the nature of its principal skeleton and substituent groups. The following shows its typical production process.

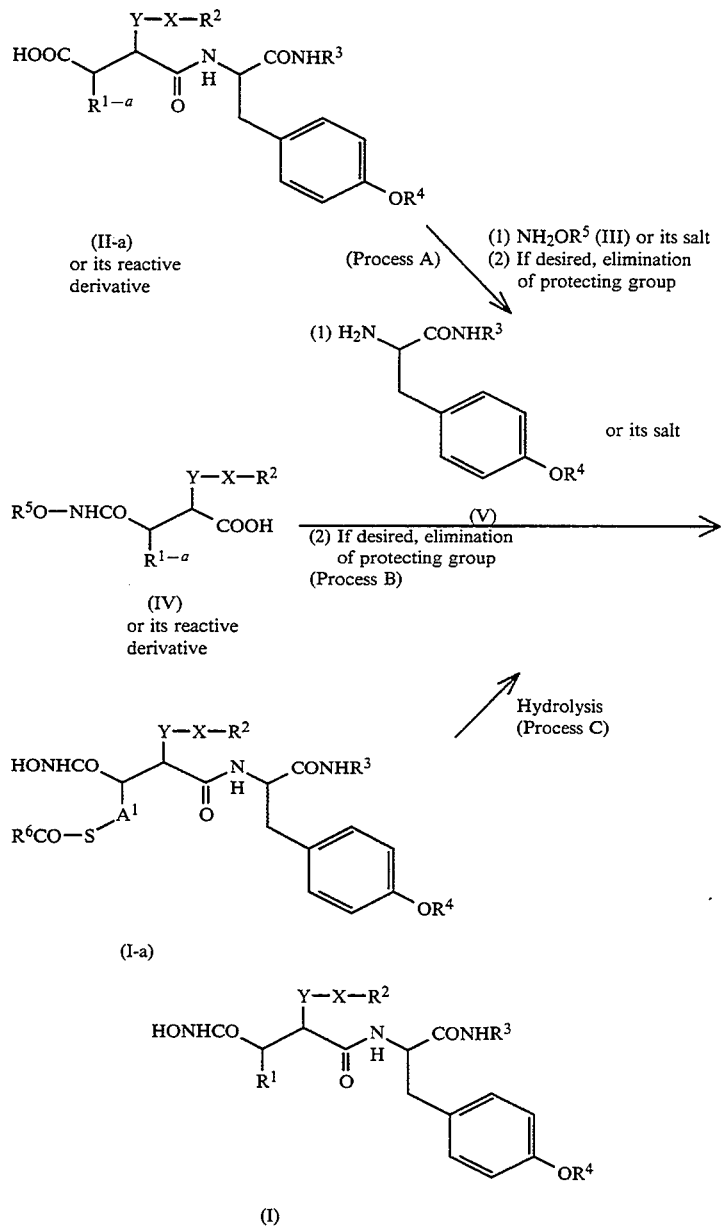

(In the above formulae, $R^1$, $R^2$, $R^3$, $R^4$, X and Y have the same respective meanings as described in the foregoing, $R^{1-a}$ represents the same group of $R^1$ excluding a lower alkyl group substituted by a mercapto group, $R^5$ represents a hydrogen atom or a protecting group, $R^6$ represents a hydrogen atom or a $C_{1-5}$ alkyl group and $A^1$ represents a lower alkylene group)

The compound (I) of the present invention, excluding a case in which $R^1$ is a lower alkyl group substituted by a mercapto group, can be obtained by a process in which a corresponding carboxylic acid (II-a) or its reactive derivative is allowed to react with an optionally protected hydroxylamine compound represented by the general formula (III), or a salt thereof, followed by the elimination of the protecting group if desired (Process A) or by a process in which an optionally protected carboxylic acid represented by the general formula (IV) or its reactive derivative is allowed to react with an amine compound represented by the general formula (V) or a salt thereof, followed by the elimination of the protecting group if desired (Process B) or, when $R^1$ is a mercapto lower alkyl group, by a process in which a corresponding acylthio-lower alkyl group-containing compound (I-a) is hydrolyzed (Process C).

The following describes each of these production processes in detail.

Process A

A conventional method for the production of a hydroxamic acid from a carboxylic acid or its reactive derivative is applied to this process.

Examples of reactive derivatives of the compound (II-a) include: usual esters such as methyl ester, ethyl ester, isobutyl ester, tert-butyl ester, benzyl ester, p-methoxybenzyl ester and the like; acid halides such as acid chloride and the like; active esters obtained by a reaction with phenol compounds such as p-nitrophenol and the like or with N-hydroxylamine compounds such as 1-hydroxysuccinimide, 1-hydroxybenzotriazole (HOBT) and the like; symmetric acid anhydrides; and organic acid-based mixed acid anhydrides obtained by a reaction with alkyl carbonic acid, p-toluenesulfonic acid and other organic acid, and phosphoric acid-based mixed acid anhydrides obtained by a reaction with diphenylphosphoryl chloride and N-methylmorpholine; of which the use of an alkylcarbonic acid mixed acid anhydride is particularly advantageous because a compound of interest can be obtained easily.

When a free carboxylic acid (II-a) is used, the reaction may be carried out in the presence of a condensing agent such as dicyclohexylcarbodiimide (DCC) or the like.

Though it may depend on the reactive derivative used, it is advantageous to carry out the reaction using the compound (II-a) or its reactive derivative and the hydroxylamine compound which may be protected or a salt thereof in the equivalent or slightly altered molar ratio, with cooling or at room temperature in an inert organic solvent such as N,N-dimethylformamide, N,N-dimethylacetamide, dimethyl sulfoxide, ether, dioxane, tetrahydrofuran, dichloromethane, dichloroethane, chloroform or the like or in a mixed solvent thereof.

In some cases, it is advantageous to add a base such as N-methylmorpholine, trimethylamine, triethylamine, N,N-dimethylaniline, pyridine, picoline, lutidine, Triton B or the like for the smooth progress of the reaction.

Examples of the protecting groups to be used are protecting groups for a hydroxyl group which include benzyl-based protecting groups including a benzyl group and substituted benzyl groups such as 2,6-dichlorobenzyl group, 2-nitrobenzyl group and the like and acyl-based protecting groups such as a benzyloxycarbonyl group and the like, and these protecting groups can be removed easily by catalytic reduction. Benzyl-based protection groups may be removed also by acid treatment and the acyl-based protecting groups may be removed also by alkali saponification.

Process B

In this process, an amide compound is produced from a carboxylic acid or a derivative thereof, and any of the conventional amide or peptide forming reactions can be applied to this process.

Examples of the reactive derivatives to be used in this process include: acid halides such as acid chloride, acid bromide and the like; acid azides; active esters similar to those used in the Process A; symmetric acid anhydrides; and mixed acid anhydrides similar to those used in the Process A.

When the compound (IV) is allowed to react in the form of free acid or the aforementioned active ester, the reaction may be carried out in the presence of a condensing agent such as the aforementioned DCC, or carbonyldiimidazole, diphenylphosphoryl azide, diethylphosphoryl cyanide or the like.

Especially, in the case of the present invention, it is advantageous to carry out]the reaction in the coexistence of an active ester and a condensing agent, such as the HOBT-DCC method.

It is advantageous to carry out the reaction using the compound (IV) or its reactive derivative and the compound (V) or a salt thereof in the almost equivalent or slightly altered molar ratio, generally with cooling or at room temperature in an organic solvent selected mostly from those used in the hydroxamic acid production process A.

Similar to the case of the production process A, addition of a base is advantageous in some cases for the smooth progress of the reaction.

The protecting groups and their elimination method described in the production process A can be used in this process.

Process C

This process is a hydrolysis reaction of a thioester and can be effected by the treatment with aqueous solution of an alkali compound such as sodium hydroxide, potassium hydroxide, sodium carbonate, sodium bicarbonate, ammonium hydroxide, ammonium carbonate, ammonium carbamate or the like.

Other production processes

The compound (I) of the present invention can be produced also by the substituent-conversion methods other than the above process C. The following describes major substituent-conversion methods.

(1) Reduction

A compound whose $R^1$ is a lower alkyl group can be produced by reducing its corresponding compound whose $R^1$ is a lower alkenyl group or a lower alkylidene group. This type of reduction may be effected by hydrogenation preferably through a catalytic reduction treatment in the presence of palladium-carbon or the like catalyst. The catalytic reduction may be carried out at room temperature or with heating in an inert solvent such as toluene, methanol, ethanol or the like.

(2) Addition a. A compound whose $R^1$ is a lower alkylthio lower alkyl group, an arylthio-lower alkyl group or a lower acylthio-lower alkyl group can be obtained by effecting addition of a corresponding lower alkyl mercaptan, aryl mercaptan or thio-lower alkanoic acid to its corresponding compound whose $R^1$ is a lower alkenyl group or a lower alkylidene group, at room temperature in the presence or absence of an inert solvent such as methanol or the like.

b. A compound whose Y is a single bond and X is a sulfur atom can be produced by effecting addition of a corresponding lower alkyl mercaptan to an alkenoic acid amide derivative having a partial structure

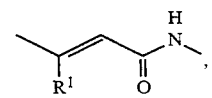

in the same manner as the case of the above procedure a.

(3) Etherification or thioetherification a. The compound (I) of the present invention can be produced by employing conventional etherification or thioetherification reaction in which a compound having a partial structure

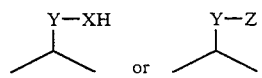

(Z: a halogen atom) is allowed to react with $R_2$—Z (Z: the same as described above) or $R_2$—XH in the presence of a base such as sodium hydride or the like.

b. A compound whose $R^1$ is a lower alkylthio-lower alkyl group or an arylthio-lower alkyl group can be produced also by the reaction of corresponding thiol and halide in the same manner as the above procedure a.

On the other hand, the intermediate (II) can be produced in accordance with a procedure which will be described later in Reference Examples or by a modified procedure thereof.

Reaction products obtained by the above procedures are isolated and purified as free compounds, salts thereof, hydrates thereof or solvates thereof. Salts can be produced by the conventional salt formation reaction.

Isolation and purification can be effected by usual chemical operations such as extraction, concentration, distillation, crystallization, filtration, recrystallization, various chromatographic techniques and the like.

Each stereoisomer, diastereomer mixture and the like can be separated in the usual way such as fractional crystallization, chromatography or the like.

INDUSTRIAL APPLICABILITY

Since the compound (I) of the present invention, pharmaceutically acceptable salts thereof, pharmaceutically acceptable hydrates thereof and the like have excellent matrix metalloprotease inhibitory activities and their efficacy can be confirmed in rabbit osteoarthritis model, they are useful for the prevention and treatment of diseases caused mainly by the progress of connective tissue destruction in human and warm-blooded animals, arthritis (e.g., chronic articular rheumatism and osteoarthritis), periodontal disease, corneal ulcer, epidermolysis bullosa, neoplastic infiltration, abnormal bone resorption and the like.

Also, the compound (II) is useful as a production intermediate of the aforementioned useful compound (I). Reaction pathway for the production of the compound (I) from the compound (II) is evident from descriptions in the aforementioned production processes and in the Reference Examples.

The matrix metalloprotease inhibitory activity of the compound of the present invention was confirmed based on its activity to inhibit collagenase.

The collagenase inhibitory activity was measured by the following procedure.

(1) Measurement of collagenase inhibitory activity

A 10 mg/ml suspension of *M. butyricum* (in liquid paraffin) was administered in a dose of 0.1 ml to the base of the tail of a Lewis rat and, 3 to 4 weeks thereafter, a periosteum tissue sample including patella was collected from a knee joint of the adjuvant arthritis rat. The thus collected tissue was cultured for 2 days using a 0.2% lactalbumin MEM medium. Collagenase inhibitory activity in the resulting culture supernatant was measured using fluorescence-labeled collagen in accordance with the procedure of Nagai et al. [cf. *Inflammation*, 4 (2), 123 (1984)].

Collagenase in the culture supernatant was activated with trypsin which was subsequently inactivated with excess amount of a soybean trypsin inhibitor. After adding the inhibitor, the substrate collagen was added to the supernatant and the mixture was incubated at 36° C. After 2 to several hours of the incubation, the reaction was terminated with ethylenediaminetetraacetic acid (EDTA), and the degradation product of collagen was extracted with 70% ethanol. The extract was subjected to centrifugation and the fluorescence intensity of the extracted degradation product was measured at 520 nm (Em)/495 nm (Ex).

As the result, almost all of the compounds disclosed in Examples showed a collagenase activity ($IC_{50}$ value) of $10^{-9}$ to $10^{-10}$ M.

(2) Osteoarthritis model

Evaluation in the rabbit osteoarthritis model is carried out in accordance with the procedures disclosed in *Arthritis and Rheumatism* 26, 875, (1983), ibid. 26, 1132 (1983) and ibid. 26, 1380 (1983).

Efficacy of the compound of the present invention can be confirmed by this rabbit osteoarthritis model test.

The pharmaceutical composition which contains as an active ingredient at least one of the compound represented by the general formula (I), pharmaceutically acceptable salts thereof, pharmaceutically acceptable hydrates thereof and the like may be made into tablets, powders, fine granules, granules, capsules, pills, solutions, injections, suppositories, ointments, plasters and the like using usually used carriers, vehicles and other additives, and the resulting preparations may be administered orally (including sublingual administration) or parenterally (including intraarticular injection).

Clinical dose of the compound of the present invention for human may be decided optionally depending on the symptom, weight, age, sex distinction and the like of each patient, but the daily dose per adult may be in the range of generally from 10 to 500 mg, preferably from 100 to 500 mg, in the case of oral administration, or generally from 1 to 100 mg, preferably from 10 to 100 mg, in the case of parenteral administration, which may be administered once a day or dividing the daily dose into several times. Since the dose changes under various conditions, sufficient effects may be obtained in some cases by a smaller dose than the above range.

Tablets, powders, granules and the like may be used as solid compositions of the present invention for use in the oral administration. In these solid compositions, at least one active ingredient is mixed with at least one inert diluent such as lactose, mannitol, glucose, hydroxypropyl cellulose, microcrystalline cellulose, starch, polyvinyl pyrrolidone, magnesium metasilicate aluminate or the like. In the usual way, the composition may contain various additives other than the inert diluent, which include a lubricant such as magnesium stearate, a disintegrating agent such as calcium carboxymethylcellulose, a stabilizing agent such as lactose and a solution adjuvant such as glutamic acid or aspartic acid. If necessary, tablets or pills may be coated with gastric or enteric films such as of sucrose, gelatin, hydroxypropyl cellulose, hydroxypropyl methyl cellulose phthalate and the like.

Examples of the liquid composition for use in oral administration include pharmaceutically acceptable emulsions, solutions, suspensions, medicated syrups, elixirs and the like, which contain generally used inert diluents such as purified water and ethanol. In addition to the inert diluent, this composition may also contain adjuvants such as a solubilizer or a solution adjuvant, a moistening agent, a suspending agent, a sweetener, a flavoring agent, an aromatic agent and an antiseptic agent.

Injections for use in parenteral administration include aseptic aqueous or non-aqueous solutions, suspensions and emulsions. Examples of the medium of aqueous solutions and suspensions include distilled water for injection use and physiological saline. Examples of the medium of non-aqueous solutions and suspensions include propylene glycol, polyethylene glycol, plant oils such as olive oil, alcohols such as ethanol, Polysolvate 80 (trade name) and the like. Such compositions may further contain additives such as a isotonicity agent, an antiseptic agent, a moistening agent, an emulsifying agent, a dispersing agent, a stabilizing agent (for example, lactose) and a solubilizer or a solution adjuvant. Sterilization of these compositions may be effected by filtration through a bacterial filter, blending of a bactericide or irradiation. Alternatively, a liquid composition may be prepared by firstly preparing an aseptic solid composition and dissolving it in sterile water or aseptic solvent for injection use before its use.

BEST MODE FOR CARRYING OUT THE INVENTION

The following examples are provided to further illustrate the present invention. In this instance, processes for the production of the intermediate to be used in the examples are described in reference examples.

In the following examples and reference examples, Tr means a trityl group, Bzl means a benzyl group, tBu means a tert-butyl group, iBu means an isobutyl group, HOBT means 1-hydroxybenzotriazole and DCC means dicyclohexylcarbodiimide.

Reference Example 1

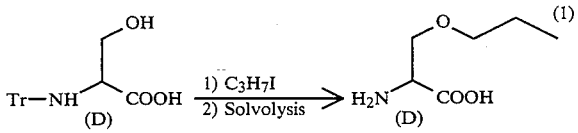

To a mixed solution consisting of 10 g of 60% sodium hydride, 0.35 g of imidazole and 90 ml of dry tetrahydrofuran was added at −15° C. a mixed solution consisting of 8.3 g of N-trityl-D-serine and 50 ml of tetrahydrofuran in a dropwise manner spending 15 minutes, followed by 45 minutes of stirring at −15° C. To this was added 32 g of propyl iodide, followed by 2 hours of stirring at −5° C. To the resulting mixture cooled at −15° C. were further added 4.0 g of 60% sodium hydride and 64 g of propyl iodide, followed by overnight stirring at −5° C. The thus obtained reaction solution was mixed with 400 ml of water and extracted twice with 100 ml of ether.

The resulting water layer was neutralized with glacial acetic acid and extracted twice with 120 ml of ether. The ether layers were combined, washed with 5% citric acid aqueous solution and saturated sodium chloride aqueous solution, dried and then concentrated to obtain an oily material. To this was added 36 ml of a 10% acetic acid-ethanol solution, followed by overnight stirring at room temperature. Thereafter, the thus formed precipitate was collected by filtration and washed with ethanol and ether to obtain 3.2 g of O-propyl-D-serine.

Physicochemical properties

Mass spectrometric data (m/z) (EI): 147 (M+) Nuclear magnetic resonance spectrum (D$_2$O, TMS internal standard) δ: 0.87 (3H, t, J=7.2 Hz), 1.46–1.69 (2H, m), 3.51 (2H, t, J=6.7 Hz), 3.87 (2H, m)

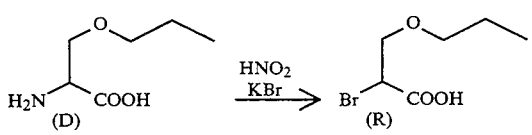

To a mixed solution consisting of 11.5 g of O-propyl-D-serine, 32.7 g of potassium bromide and 60 ml of 23% sulfuric acid was added at −5° C. 7.12 g of sodium nitrite which has been dissolved in 70 ml of water, in a dropwise manner spending 1 hour. After 5 hours of stirring at 0° C., the resulting reaction solution was extracted four times with 100 ml of methylene chloride, i dried and then concentrated to obtain 12.9 g of 2R-bromo-3-propoxypropionic acid. Physicochemical properties Mass spectrometric data (m/z) (EI): 211 (M+) Nuclear magnetic resonance spectrum (CDCl$_3$, TMS internal standard) δ: 0.91 (3H, t, J=7.3 Hz), 1.41–1.71 (2H, m), 3.50 (2H, t, J=6.5 Hz), 3.85 (2H, m), 4.35 (1H, m)

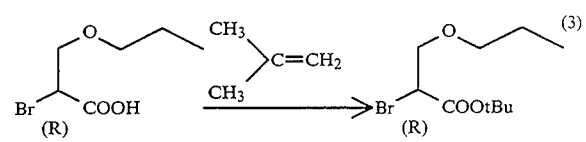

To a mixed solution consisting of 16.4 g of 2R-bromopropoxypropionic acid and 50 ml of methylene chloride were added at −40° C. the same volume of isobutene and 2 ml of concentrated sulfuric acid, followed by sealing and subsequent overnight stirring at room temperature. The resulting reaction solution was concentrated to a ½ volume, and the methylene chloride layer was washed twice with 10% sodium carbonate aqueous solution, dried and then concentrated to obtain 18.2 g of tert-butyl 2R-bromo-3-propoxypropionate.
Physicochemical properties Nuclear magnetic resonance spectrum (CDCl$_3$, TMS internal standard) δ: 0.91 (3H, t, J=7.3 Hz), 1.47 (9H, s), 1.46–1.60 (2H, m), 3.46 (2H, t, J=6.6 Hz), 3.79 (2H, m), 4.20 (1H, m)

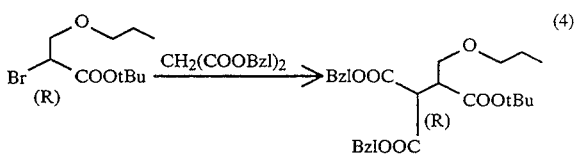

With cooling on an ice bath, 7.65 g of potassium tert-butoxide was added to a mixed solution consisting of 19.4 g of dibenzyl malonate and 70 ml of N,N-dimethylformamide. At 0° C., to this was added a mixed solution consisting of tert-butyl 2R-bromo-3-propoxypropionate and 30 ml of N,N-dimethylformamide in a dropwise manner spending 1 hour, followed by overnight stirring at a temperature of 5° C. or lower. The resulting reaction solution was mixed with saturated ammonium chloride aqueous solution, extracted four times with 100 ml of ethyl acetate, dried and then concentrated to obtain 29.5 g of benzyl [2-benzyloxycarbonyl-3R-(tert-butoxycarbonyl)-4-propoxy]butylate.
Physicochemical properties Mass spectrometric data (m/z) (FAB): 471 (M+ +1) Nuclear magnetic resonance spectrum (CDCl$_3$, TMS internal standard) δ: 0.84 (3H, t, J=7.7 Hz), 1.39 (9H, s), 1.46–1.50 (2H, m), 3.25 (2H, t, J=7.0 Hz), 3.48 (1H, s), 3.60 (2H, m), 4.01 (1H, d, J=9.0 Hz), 5.11–5.17 (4H, m), 7.26–7.34 (10H, m)

Reference Example 2

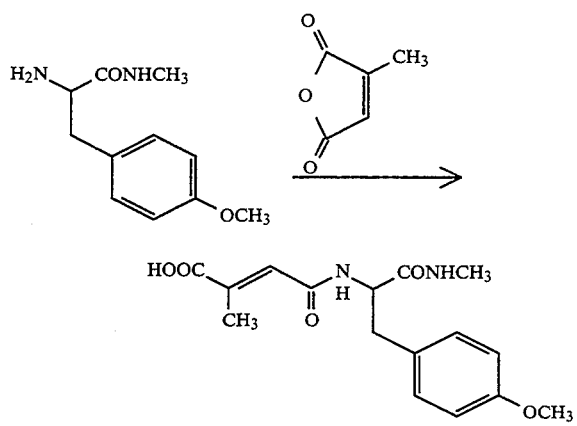

A mixed solution consisting of 50 g of N,O-dimethyltyrosine amide, 400 ml of dry chloroform and 27 g of citraconic anhydride was stirred at room temperature for 6 hours, concentrated under a reduced pressure, subjected to a silica gel column chromatography and eluted with chloroform-methanol-acetic acid to obtain 20 g of $N^{\alpha}$-(3-carboxy-2-butenoyl)-N,O-dimethyltyrosine amide.

Physicochemical properties

Mass spectrometric data (m/z) (FAB): 321 (M$^+$+1)
Nuclear magnetic resonance spectrum (DMSO-d$_6$, TMS internal standard) δ: 1.73 (3H, s), 2.59 (1H, m), 2.64 (3H, d, J=4 Hz), 3.20 (1H, m), 3.70 (3H, s), 4.27–4.33 (1H, m), 5.74 (1H, s), 6.82 (2H, d, J=6.8 Hz), 7.12 (2H, d, J=6.8 Hz), 7.81 (1H, d, J=2 Hz), 8.46 (1H, d, J=7.2 Hz), 12.80 (1H, br)

Reference Example 3

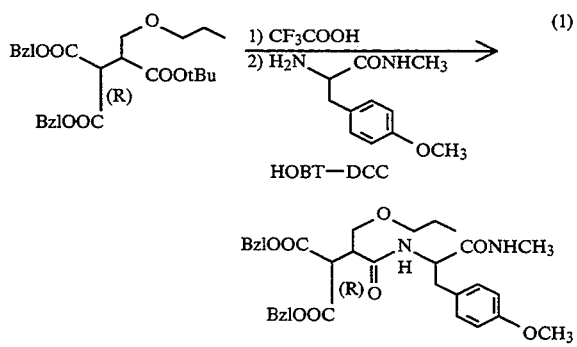

A mixed solution consisting of 29.0 g of benzyl [2-benzyloxycarbonyl-3R-(tert-butoxycarbonyl)-4-propoxy]butylate and 50 ml of 95% trifluoroacetic acid aqueous solution was stirred overnight at a temperature of 5° C. or lower. The resulting reaction mixture was concentrated to obtain 25.5 g of an oily material. With cooling on an ice bath, to a mixed solution consisting of this oily material, 9.88 g of 1-hydroxybenzotriazole, 7.47 g of N-methylmorpholine, 15.3 g of O-methyltyrosine N-methylamide and 150 ml of N,N-dimethylformamide was added another mixed solution consisting of 15.2 g of dicyclohexylcarbodiimide and 150 ml of tetrahydrofuran in a dropwise manner, followed by overnight stirring at room temperature.

After concentration, ethyl acetate was added to the reaction mixture, the resulting organic layer was washed with 10% citric acid aqueous solution, saturated sodium bicarbonate aqueous solution and saturated sodium chloride aqueous solution, dried and concentrated. The thus obtained residue was subjected to a silica gel column chromatography and elution was carried out with chloroform to obtain 25.0 g of $N^{\alpha}$-[[3,3-bis(benzyloxycarbonyl)-2R-propoxymethyl]propionyl]-N,O-dimethyltyrosine amide.

Physicochemical properties

Mass spectrometric data (m/z) (FAB): 606 (M$^+$+1)
Nuclear magnetic resonance spectrum (CDCl$_3$, TMS internal standard) δ: 0.78 (3H, t, J=7.7 Hz), 1.24–1.36 (2H, m), 2.69 (3H, d, J=5.0 Hz), 3.78 (3H, s), 4.60 (1H, m), 5.09–5.16 (4H, m), 6.30 (1H, s), 6.55 (1H, d, J=8.5 Hz), 6.82 (2H, d, J=8.5 Hz), 7.10 (2H, d, J=8.5 Hz), 7.26–7.32 (10H, m)

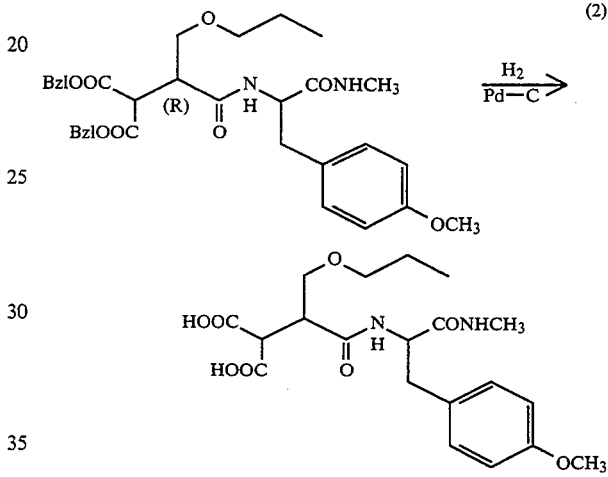

A mixed solution consisting of 300 mg of $N^{\alpha}$-[[3,3-bis(benzyloxycarbonyl)-2-R-propoxymethyl]propionyl]-N,O-dimethylyrosine amide, 5 ml of methanol and 50 mg of 10% palladium-carbon catalyst was put into a reaction vessel and, after replacing the atmosphere in the vessel by hydrogen gas, stirred at room temperature for 2 hours. After removing the catalyst by filtration, the resulting reaction solution was concentrated to obtain 190 mg of $N^{\alpha}$-[(3,3-biscarboxy-2-propoxymethyl)propionyl]-N,O-dimethyltyrosine amide.

Physicochemical properties

Mass spectrometric data (m/z) (FAB): 425 (M$^+$+1)
Nuclear magnetic resonance spectrum (DMSO-d$_6$, TMS internal standard) δ: 0.73–0.85 (3H, m), 1.31–1.46 (2H, m), 2.60 (3H, d, J=4.4 Hz), 3.70 (3H, s), 4.66 (1H, m), 6.82 (2H, d, J=7.8 Hz), 7.12 (2H, d, J=7.8 Hz), 7.86 (1H, d, J=4.4 Hz)

Reference Example 4

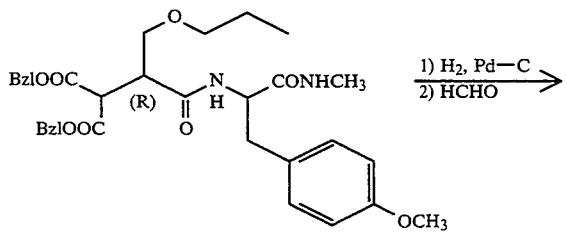

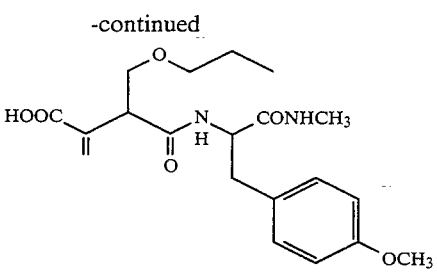

A mixed solution consisting of 4.9 g of N$^\alpha$-[[3,3-bis(-benzyloxycarbonyl)-2-R-propoxymethyl]propionyl]-N,O-dimethyltyrosine amide, 2.55 g of ammonium formate, 1.0 g of palladium-carbon catalyst and 70 ml of 10% ethanol was put into a reaction vessel and, after replacing the atmosphere in the vessel by hydrogen gas, stirred at room temperature for 1 hour. After removing the catalyst by filtration, the resulting filtrate was mixed with 0.76 g of piperidine, stirred at room temperature for 30 minutes, mixed with 3.8 ml of 35% formaldehyde aqueous solution and then stirred overnight at room temperature.

After 1 hour of heating under reflux, the resulting reaction solution was concentrated, mixed with 10% citric acid aqueous solution and then extracted three times with ethyl acetate. The resulting organic layer was extracted with potassium carbonate aqueous solution, and the water layer was adjusted to pH 4 with hydrochloric acid and extracted again with methylene chloride. The resulting methylene chloride extract was dried and concentrated to obtain 1.5 g of N$^\alpha$-[(3-carboxy-2-propoxymethyl)-3-butenoyl]-N,O-dimethyltyrosine amide.

Physicochemical properties

Mass spectrometric data (m/z) (FAB): 393 (M$^+$+1)
Nuclear magnetic resonance spectrum (DMSO-d$_6$, TMS internal standard) $\delta$: 0.76–0.83 (3H, m), 1.37–1.48 (2H, m), 2.57 (3H, d, J=4.8 Hz), 3.70 (3H, s), 4.38 (1H, m), 5.53, 6.06 (2H, s), 6.77 (2H, d, J=8.4 Hz), 7.05 (2H, d, J=8.4 Hz), 7.71 (1H, d, J=4.8 Hz), 7.98 (1H, d, J=8.8 Hz), 12.60 (1H, s)

Reference Example 5

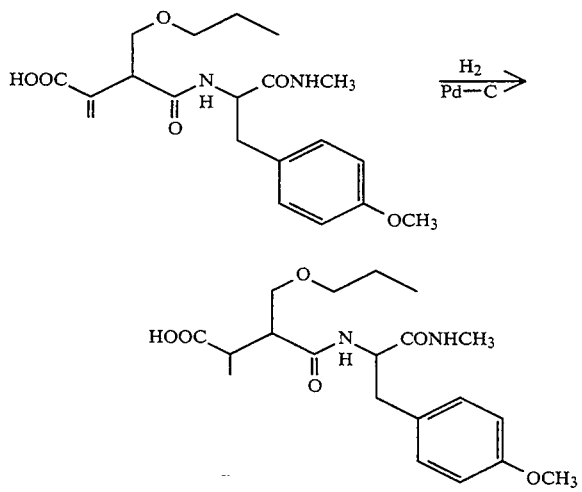

A mixed solution consisting of 500 mg of N$^\alpha$-[(3-carboxy-2-propoxymethyl)-3-butenoyl]-N,O-dimethyltyrosine amide, 10 ml of methanol and 50 mg of palladium-carbon catalyst was put into a reaction vessel and, after replacing the atmosphere in the vessel by hydrogen gas, stirred at room temperature for 5 hours. After removing the catalyst by filtration, the resulting filtrate was concentrated to obtain 470 mg of N$^\alpha$-[(3-carboxy-2-propoxymethyl)butylyl]-N,O-dimethyltyrosine amide.

Physicochemical properties

Mass spectrometric data (m/z) (FAB): 395 (M$^+$+1)
Nuclear magnetic resonance spectrum (DMSO-d$_6$, TMS internal standard) $\delta$: 0.59 (3H, d, J=6.8 Hz), 0.74–0.86 (3H, m), 1.40–1.45 (2H, m), 2.58 (3H, d, J=4.4 Hz), 3.69 (3H, s), 4.43 (1H, m), 6.80 (2H, d, J=8.8 Hz), 7.14 (2H, d, J=8.8 Hz), 7.49 (1H, d, J=4.4 Hz), 8.31 (1H, d, J=8.8 Hz)

Reference Example 6

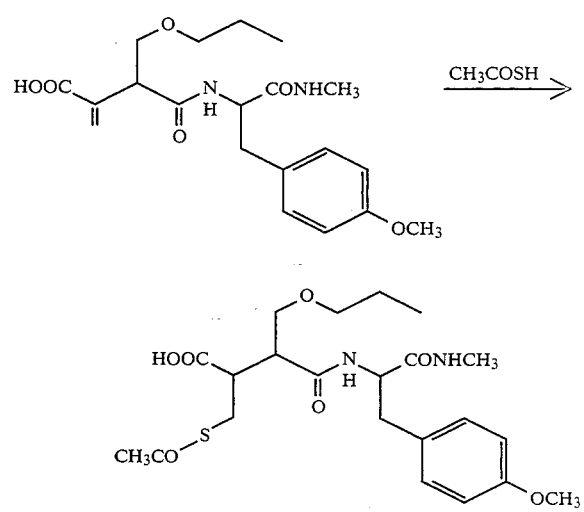

A mixed solution consisting of 1.0 g of N$^\alpha$-[(3-carboxy-2-propoxymethyl)-3-butenoyl]-N,O-dimethyltyrosine amide and 6 ml of thioacetic acid was stirred overnight at room temperature. After concentration, the resulting residue was washed with ether to obtain 0.8 g of N$^\alpha$-[(3-carboxy-4-acetylthio-2-propoxymethyl)-butylyl]-N,O-dimethyltyrosine amide.

Physicochemical properties

Mass spectrometric data (m/z) (FAB): 469 (M$^+$+1)
Nuclear magnetic resonance spectrum (DMSO-d$_6$, TMS internal standard) $\delta$: 0.78–0.82 (3H, m), 1.39–1.44 (2H, m), 2.25 (3H, s), 2.58 (3H, d, J=4.4 Hz), 3.65 (3H, s), 6.74 (2H, d, J=8.8 Hz), 7.13 (2H, d, J=8.8 Hz), 7.59 (1H, d, J=4.9 Hz), 8.40 (1H, d, J=8.8 Hz) Melting point: 185°–186° C. (recrystallization from methanol)

| Elemental analysis value (as C$_{22}$H$_{32}$N$_2$O$_7$S.½H$_2$O) | | | |
|---|---|---|---|
| | C(%) | H(%) | N(%) | S(%) |
| Anal.: | 55.33 | 6.96 | 5.87 | 6.71 |
| Found: | 55.54 | 6.72 | 5.82 | 6.91 |

Reference Example 7

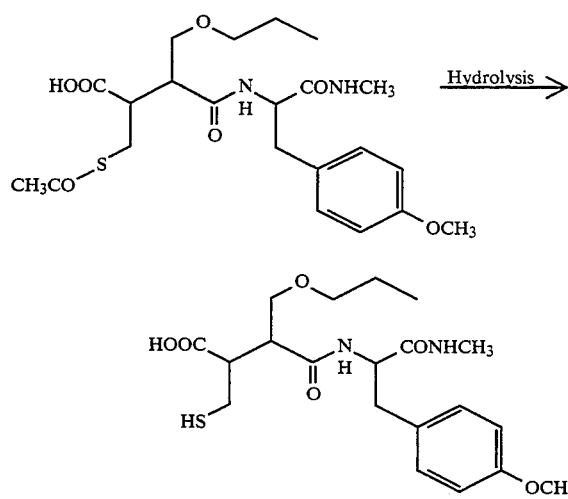

A 200 mg portion of N$^\alpha$-[(3-carboxy-4-acetylthio-2-propoxymethyl)butylyl]-N,O-dimethyltyrosine amide was dissolved in 10 ml of methanol. Argon gas was bubbled into the resulting solution during addition of 0.86 ml of 1N sodium hydroxide aqueous solution and subsequent 2 hours of stirring at room temperature. After addition of 1 ml of 1N hydrochloric acid and subsequent concentration, water was added to the concentrated solution and the thus formed precipitate was collected by filtration to obtain 130 mg of N$^\alpha$-[(3-carboxy-4-mercapto-2-propoxymethyl)butylyl]-N,O-dimethyltyrosine amide.

Physicochemical properties

Mass spectrometric data (m/z) (FAB): 428 (M$^+$+1)
Nuclear magnetic resonance spectrum (DMSO-d$_6$, TMS internal standard) δ: 0.78–0.82 (3H, m), 1.39–1.46 (2H, m), 2.59 (3H, d, J=4.4 Hz), 3.72 (3H, s), 6.82 (2H, d, J=8.8 Hz), 7.15 (2H, d, J=8.4 Hz), 7.54 (2H, d, J=4.9 Hz), 8.40 (1H, d, J=8.8 Hz)

Reference Example 8

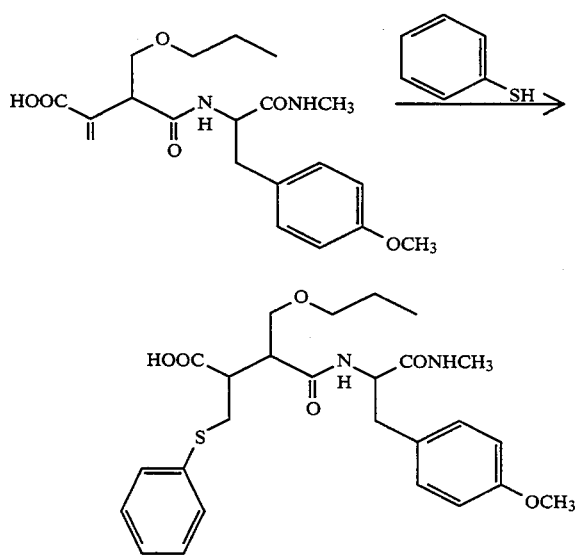

A mixed solution consisting of 1.0 g of N$^\alpha$-[(3-carboxy-2-propoxymethyl)-3-butenoyl]-N,O-dimethyltyrosine amide and 5 ml of thiophenol was stirred at 60° C. for 2 days in the dark. After adding ether, the resulting precipitate was collected by filtration and washed with ether to obtain 200 mg of N$^\alpha$-[(3-carboxy-4-phenylthio-2-propoxymethyl)butylyl]-N,O-dimethyltyrosine amide.

Physicochemical properties

Mass spectrometric data (m/z) (FAB): 504 (M$^+$+1)
Nuclear magnetic resonance spectrum (DMSO-d$_6$, TMS internal standard) δ: 0.78–0.82 (3H, m), 1.38–1.46 (2H, m), 2.60 (3H, d, J=4.4 Hz), 3.68 (3H, s), 6.71 (2H, d, J=8.8 Hz), 6.99 (2H, d, J=8.4 Hz), 7.64 (1H, d, J=4.9Hz), 8.50 (1H, d, J=8.8 Hz)

Reference Example 9

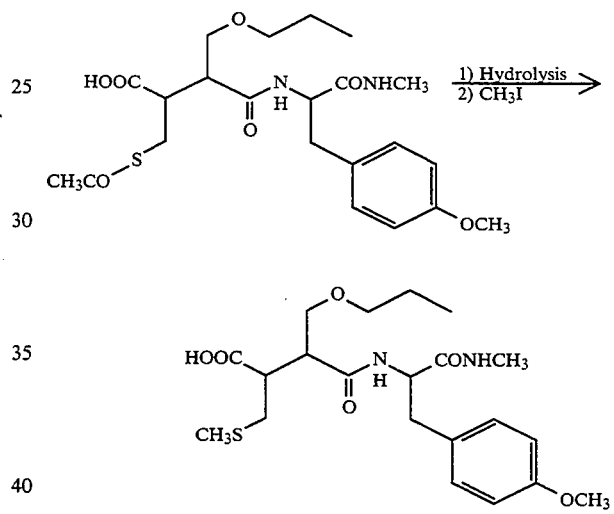

Into a mixed solution consisting of 800 mg of N$^\alpha$-[(3-carboxy-4-acethylthio-2-propoxymethyl)butylyl]-N,O-dimethyltyrosine amide and 10ml of methanol was bubbled argon gas during addition of 8.5 ml of 1N sodium hydroxide aqueous solution and subsequent 30 minutes of stirring. To the resulting mixture was added 0.97 g of methyl iodide, followed by additional 2 hours of stirring. After addition of 10 ml of 1N hydrochloric acid and subsequent concentration, water was added to the concentrated solution and the thus formed precipitate was collected by filtration to obtain 650 mg of N$^\alpha$-[(3-carboxy-4-methylthio-2-propoxymethyl)butylyl]-N,O-dimethyltyrosine amide.

Physicochemical properties

Mass spectrometric data (m/z) (FAB): 441 (M$^+$+1)
Nuclear magnetic resonance spectrum (DMSO-d$_6$, TMS internal standard) δ: 0.79–0.83 (3H, t, J=7.2 Hz), 1.36–1.46 (2H, m), 2.59 (3H, d, J=4.4 Hz), 3.39 (3H, s), 3.68 (3H, s), 6.81 (2H, d, J=8.8 Hz), 7.16 (2H, d, J=8.8 Hz), 7.54 (1H, d, J=4.4 Hz), 8.43 (1H, d, J=9.1 Hz)

Reference Example 10

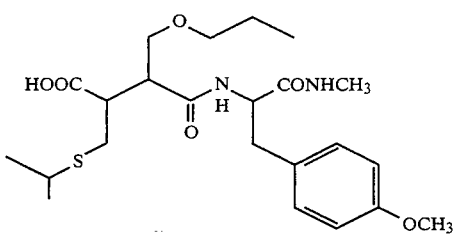

A 800 mg portion of $N^\alpha$-[(3-carboxy-4-acethylthio-2-propoxymethyl)butylyl]-N,O-dimethyltyrosine amide was treated in the same manner as described in Reference Example 9 to obtain 730 mg of $N^\alpha$-[(3-carboxy-4-isopropylthio-2-propoxymethyl)butylyl]-N,O-dimethyltyrosine amide.

Physicochemical properties

Mass spectrometric data (m/z) (FAB): 470 (M+ +1)
Nuclear magnetic resonance spectrum (DMSO-d6, TMS internal standard) δ: 0.79–0.83 (3H, t, J=7.3 Hz), 0.96, 1.02 (6H, d, J=6.3 Hz), 1.40–1.45 (2H, m), 2.60 (3H, d, J=3.4 Hz), 3.71 (3H, s), 6.80 (2H, d, J=8.3 Hz), 7.17 (2H, d, J=8.3 Hz), 7.54 (1H, s), 8.46 (1H, d, J=8.8 Hz)

Reference Example 11

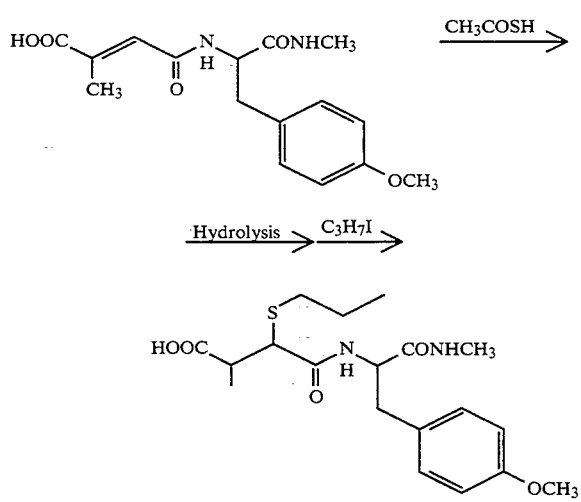

A mixed solution consisting of 20 g of $N^\alpha$-(3-carboxy-2-butenoyl)-N,O-dimethyltyrosine amide and 80 ml of thioacetic acid was stirred at room temperature for 3 days in an atmosphere of argon. The reaction solution was concentrated under a reduced pressure, and the resulting residue was mixed with 200 ml of toluene and again concentrated under a reduced pressure. The thus obtained residue was dissolved in 150 ml of methanol and cooled on an ice bath to a temperature of 10° C. or lower. To this was added 11 ml of 10N sodium hydroxide aqueous solution, followed by 2 hours of stirring in an atmosphere of argon. To this was further added 21.3 g of propyl iodide at a temperature of 10° C. or lower, followed by 3 hours of stirring. The resulting reaction solution was concentrated under a reduced pressure, 300 ml of water was added to the thus obtained residue and the thus formed precipitate was collected by filtration and dried to obtain 10 g of $N^\alpha$-[(3-carboxy-2-propylthio)butylyl]-N,O-dimethyltyrosine amide as a mixture of two isomers.

Physicochemical properties

Mass spectrometric data (m/z) (FAB): 397 (M+ +1)
Nuclear magnetic resonance spectrum (DMSO-d6, TMS internal standard) δ: 0.67–1.0 (6H, (m)), 1.29–1.49 (2H, (m)), 2.12–2.26 (1H, m), 2.40–2.60 (6H, (m)), 2.60–2.73 (1H, m), 2.86–2.90 (1H, m), 3.63–3.68 (3H, s), 4.35–4.52 (1H, m), 6.79–6.82 (2H, (m)), 7.12–7.19 (2H, (m)), 7.89 (1H, (m)), 8.34–8.39 (1H, (m)), 12.30 (1H, br s)

EXAMPLE 1

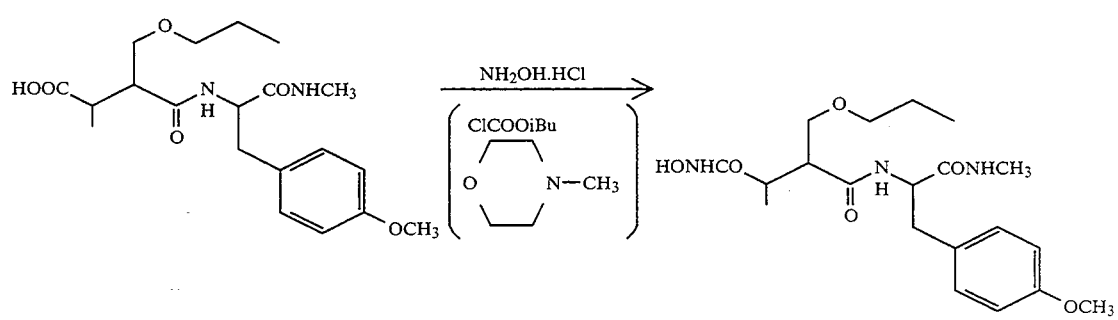

To a mixed solution consisting of 370 mg of $N^\alpha$-[(3-carboxy-2-propoxymethyl)butylyl]-N,O-dimethyltyrosine amide, 10 mg of tetrahydrofuran and 2 ml of N,N-dimethylformamide were added with cooling on an ice bath 0.20 ml of N-methylmorpholine and then 0.26 ml of isobutyl chloroformate, followed by 1 hour of stirring at the same temperature.

With cooling on an ice bath, to this was added a mixed solution consisting of 210 mg of hydroxylamine hydrochloride, 0.33 ml of N-methylmorpholine and 4 ml of N,N-dimethylformamide, followed by overnight stirring at a temperature of 5° C. or lower. After concentration, ethyl acetate and 10% potassium hydrogensulfate aqueous solution were added to the concentrated solution and the thus formed precipitate was collected by filtration to obtain 120 mg of $N^\alpha$-[[3-(N-hydroxycarbamoyl)-2-propoxymethyl]butylyl]-N,O-dimethyltyrosine amide.

Physicochemical properties

Mass spectrometric data (m/z) (FAB): 410 (M+ +1)
Nuclear magnetic resonance spectrum (DMSO-d6, TMS internal standard) δ: 0.46 (3H, d, J=6.8 Hz), 0.80–0.83 (3H, m), 1.41–1.46 (2H, m), 2.59 (3H, d, J=4.4 Hz), 3.68 (3H, s), 6.79 (2H, d, J=8.8 Hz), 7.15 (2H, d, J=8.7 Hz), 7.34 (1H, d, J=4.4Hz), 8.36 (1H, d, J=8.8 Hz), 8.75 (1H, s), 10.42 (1H, s)

EXAMPLE 2

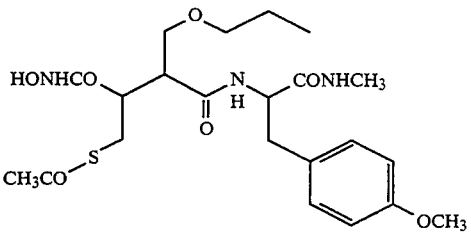

A 800 mg portion of N$^\alpha$-[(3-carboxy-4-acetylthio-2-propoxymethyl)butylyl]-N,O-dimethyltyrosine amide was treated in the same manner as described in Example 1 to obtain 680 mg of N$^\alpha$-[[3-(N-hydroxycarbamoyl)-4-acetylthio-2-propoxymethyl]butylyl]-N,O-dimethyltyrosine amide.
Physicochemical properties
Mass spectrometric data (m/z) (FAB): 484 (M$^+$+1) Nuclear magnetic resonance spectrum (DMSO-d$_6$, TMS internal standard) δ: 0.78–0.82 (3H, m), 1.39–1.44 (2H, m), 2.50 (3H, s), 2.59 (3H, d, J=4.8 Hz), 3.72 (3H, s), 6.82 (2H, d, J=8.8 Hz), 7.15 (2H, d, J=8.8 Hz), 7.54 (1H, d, J=4.4 Hz), 8.40 (1H, d, J=8.8 Hz), 8.88 (1H, s), 10.56 (1H, s)

EXAMPLE 3

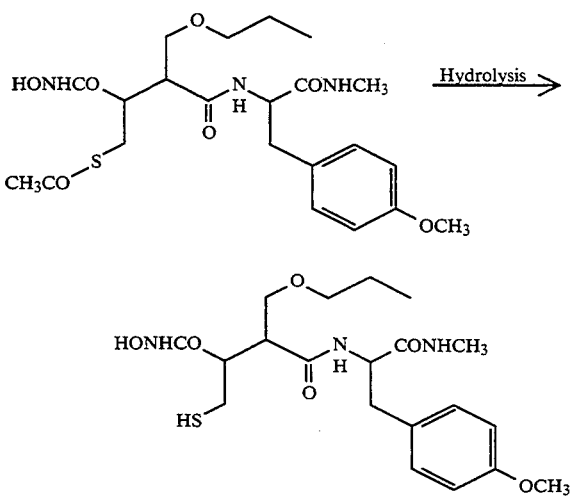

Into a mixed solution consisting of 460 mg of N$^\alpha$-[[3-(N-hydroxycarbamoyl)-4-acetylthio-2-propoxymethyl]butylyl]-N,O-dimethyltyrosine amide and 10 ml of methanol was bubbled at room temperature argon gas during addition of 4.8 ml of 1N sodium hydroxide aqueous solution and subsequent 2 hour of stirring. After addition of 5.0 ml of 1N hydrochloric acid and subsequent concentration, water was added to the concentrated solution and the thus formed precipitate was collected by filtration to obtain 210 mg of N$^\alpha$-[[3-(N-hydroxycarbamoyl)-4-mercapto-2-propoxymethyl]butylyl]-N,O-dimethyltyrosine amide.
Physicochemical properties
Mass spectrometric data (m/z) (FAB): 442 (M$^+$+1) Nuclear magnetic resonance spectrum (DMSO-d$_6$, TMS internal standard) δ: 0.79–0.82 (3H, m), 1.40–1.46 (2H, m), 2.60 (3H, d, J=4.9 Hz), 3.72 (3H, s), 6.82 (2H, d, J=9.0 Hz), 7.16 (2H, d, J=9.0 Hz), 7.38 (1H, d, J=4.8 Hz), 8.42 (1H, d, J=9.0 Hz), 8.88 (1H, s), 10.56 (1H, s)

EXAMPLE 4

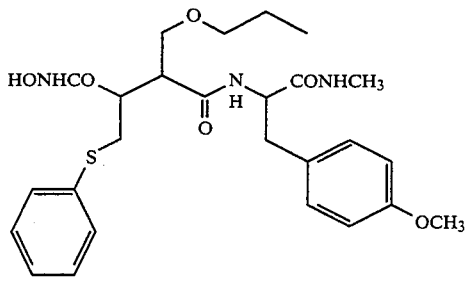

A 150 mg portion of N$^\alpha$-[(3-carboxy-4-phenylthio-2-propoxymethyl)butylyl]-N,O-dimethyltyrosine amide was treated in the same manner as described in Example 1 to obtain 90 mg of N$^\alpha$-[[3-(N-hydroxycarbamoyl)-4-phenylthio-2-propoxymethyl]butylyl]-N,O-dimethyltyrosine amide.
Physicochemical properties , Mass spectrometric data (m/z) (FAB): 518 (M$^+$+1) Nuclear magnetic resonance spectrum (DMSO-d$_6$, TMS internal standard) δ0.79–0.82 (3H, t, J=7.3 Hz), 1.40–1.46 (2H, m), 2.57 (3H, d, J=4.4 Hz), 3.67 (3H, s), 6.77 (2H, d, J=8.3 Hz), 7.14 (2H, d, J=8.3 Hz), 7.88 (1H, d, J=4.4 Hz), 8.34 (1H, d, J=8.3 Hz), 8.90 (1H, s), 10.60 (1H, s)

EXAMPLE 5

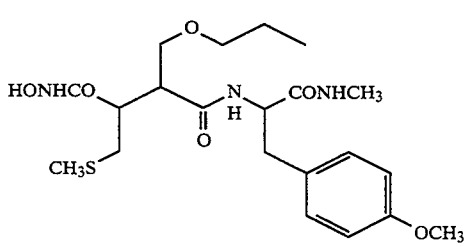

A 275 mg portion of N$^\alpha$-[(3-carboxy-4-methylthio-2-propoxymethyl)butylyl]-N,O-dimethyltyrosine amide was treated in the same manner as described in Example 1 to obtain 210 mg of N$^\alpha$-[[3-(N-hydroxycarbamoyl)-4-methylthio-2-propoxymethyl]butylyl]-N,O-dimethyltyrosine amide.
Physicochemical properties
Mass spectrometric data (m/z) (FAB): 456 (M$^+$+1) Nuclear magnetic resonance spectrum (DMSO-d$_6$, TMS internal standard) 0.80–0.83 (3H, t, J=7.1 Hz), 1.35–1.46 (2H, m), 2.61 (3H, d, J=4.0 Hz), 3.41 (3H, s), 3.71 (3H, s), 6.82 (2H, d, J=7.8 Hz), 7.17 (2H, d, J=7.8 Hz), 7.35 (1H, d, J=4.4 Hz), 8.43 (1H, d, J=9.0 Hz), 8.86 (1H, s), 10.52 (1H, s) Melting point: 252°–254° C. (recrystallization from N,N-dimethylformamide)

| | Elemental analysis value (as $C_{21}H_{33}N_3O_6S$) | | | |
|---|---|---|---|---|
| | C(%) | H(%) | N(%) | S(%) |
| Anal.: | 55.37 | 7.30 | 9.22 | 7.04 |
| Found: | 55.09 | 7.12 | 9.25 | 7.04 |

EXAMPLE 6

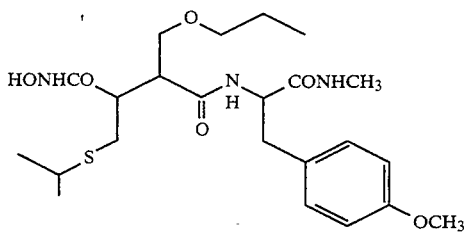

A 350 mg portion of $N^\alpha$-[(3-carboxy-4-isopropylthio-2-propoxymethyl)butylyl]-N,O-dimethyltyrosine amide was treated in the same manner as described in Example 1 to obtain 150 mg of $N^\alpha$-[[3-(N-hydroxycarbamoyl)-4-isopropylthio-2-propoxymethyl]butylyl]-N,O-dimethyltyrosine amide.

Physicochemical properties

Mass spectrometric data (m/z) (FAB): 484 (M$^+$ +1)
Nuclear magnetic resonance spectrum ( DMSO-d$_6$, TMS internal standard) δ: 0.80–0.84 (3H, t, J=7.4 Hz), 0.90, 1.00 (6H, d, J=6.6 Hz), 1.41–1.47 (2H, m), 2.60 (3H, d, J=3.4 Hz), 3.71 (3H, s), 6.79 (2H, d, J=8.3 Hz), 7.18 (2H, d, J=8.3 Hz), 7.36 (1H, d, J=4.4 Hz), 8.46 (1H, d, J=9.3 Hz), 8.85 (1H, s), 10.49 (1H, s)

EXAMPLE 7

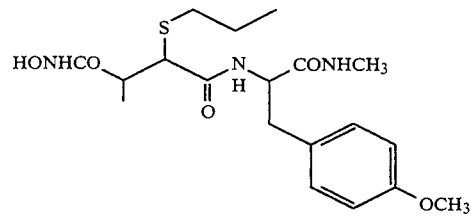

Isomer A

A 7.1 g portion of $N^\alpha$-[(3-carboxy-2-propylthio)-butylyl]-N,O-dimethyltyrosine amide was dissolved in a mixed solution consisting of 150 ml of dry tetrahydrofuran and 10 ml of N,N-dimethylformamide. In an atmosphere of argon and at a temperature of 5° C. or lower, to the thus prepared mixture were added 2.4 ml of N-methylmorpholine and then 2.8 ml of isobutyl chloroformate in a dropwise manner. After 20 minutes of stirring at a temperature of 5° C. or lower, a mixed solution consisting of 1.9 g of hydroxylamine hydrochloride, 3 ml of N-methylmorpholine and 20 ml of N,N-dimethylformamide was added to the resulting reaction mixture.

After 3 hours of stirring, the resulting reaction solution was concentrated under a reduced pressure. A 50 ml portion of dilute hydrochloric acid was added to the resulting residue to collect the thus formed precipitate by filtration. The precipitate was washed with water and ether and then dried to obtain 5.2 g of $N^\alpha$-[[3-(N-hydroxycarbamoyl)-2-propylthio]butylyl]-N,O-dimethyltyrosine amide as a mixture of two isomers. A 1 g portion of the product was subjected to a silica gel column chromatography and eluted with chloroform-methanol-acetic acid (100:2:2) to obtain 0.3 g of isomer A (and 0.3 g of isomer B) of $N^\alpha$-[[3-(N-hydroxycarbamoyl)-2-propylthio]butylyl]-N,O-dimethyltyrosine amide.

Physicochemical properties

Mass spectrometric data (m/z) (FAB): 412 (M$^+$ +1)
Nuclear magnetic resonance spectrum (DMSO-d$_6$, TMS internal standard) δ: 0.54 (3H, d, J=6.8 Hz), 0.85 (3H, t, J=7.2 Hz), 1.43 (2H, q, J=7.2Hz), 1.89–2.33 (1H, m), 2.44 (2H, t, J=7.2 Hz), 2.58 (3H, d, J=4.0 Hz), 2.65–2.71 (1H, m), 2.85–2.88 (1H, m), 3.67 (3H, s), 4.47 (1H, m), 6.79 (2H, d, J=8.4 Hz), 7.14 (2H, d, J=8.4 Hz), 7.85 (1H, d, J=4.4 Hz), 8.34 (1H, d, J=8.8 Hz), 8.75 (1H, br s), 10.43 (1H, s)

Formulation Example 1 (tablets)

|  | Contents per tablet |
| --- | --- |
| Compound of Example 5 | 10 mg |
| Lactose | 109 mg |
| Corn starch | 27.25 mg |
| Hydroxypropylcellulose | 3 mg |
| Magnesium stearate | 0.75 mg |
|  | 150 mg |

The compound of Example 5, lactose and corn starch were mixed using a mixer, and the mixture was made into granules by a fluidized-bed granulation method using an aqueous solution of hydroxypropylcellulose which has been prepared in advance. The thus obtained granules were dried at 40° C., mixed uniformly with magnesium stearate and then subjected to compression molding to obtain tablets, each weighing 150 mg.

Formulation Example 2 (tablets)

|  | Contents per tablet |
| --- | --- |
| Compound of Example 5 | 40 mg |
| Lactose | 130.5 mg |
| Corn starch | 14.5 mg |
| Hydroxypropylcellulose | 4 mg |
| Calcium carboxymethylcellulose | 10 mg |
| Magnesium stearate | 1 mg |
|  | 200 mg |

The compound of Example 5, lactose and corn starch were mixed using a mixer, and the mixture was made into granules by a fluidized-bed granulation method using an aqueous solution of hydroxypropylcellulose which has been prepared in advance. The thus obtained granules were dried at 40° C., mixed uniformly with calcium carboxymethylcellulose and magnesium stearate and then subjected to compression molding to obtain tablets, each weighing 200 mg.

What is claimed is:

1. A compound represented by the following formula (I):

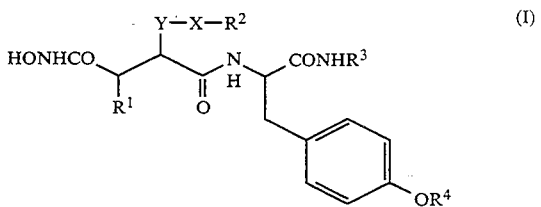

each character in this formula means as follows;

R$^1$: a lower alkyl group which may be substituted by a substituent group selected from the class consisting of a mercapto group, a lower alkylthio group, an arylthio group and a lower acylthio group, $R^2$, $R^3$ and $R^4$: the same or different from one another and each represents a lower alkyl group, X: an oxygen atom or a sulfur atom, Y: a single bond or a lower alkylene group, a pharmaceutically acceptable salt thereof, a pharmaceutically acceptable hydrate thereof, a pharmaceutically acceptable solvate thereof or a stereoisomer thereof.

2. The compound according to claim 1 wherein the group —Y—X—$R^2$ is a propoxymethyl group or a propylthio group.

3. The compound according to claim 1 wherein the group —Y—X—$R^2$ is a propoxymethyl group or a propylthio group and $R^1$ is a lower alkyl group or a lower alkylthiomethyl group.

4. $N^\alpha$-[[3-(N-hydroxycarbamoyl)-4-methylthio-2-propoxymethyl]butylyl]-N,O-dimethyltyrosine amide, a pharmaceutically acceptable salt thereof or a stereoisomer thereof.

5. $N^\alpha$-[[3-(N-hydroxycarbamoyl)-4-isopropylthio-2-propoxymethyl]butylyl]-N,O-dimethyltyrosine amide, a pharmaceutically acceptable salt thereof or a stereoisomer thereof.

6. $N^\alpha$-[[3-(N-hydroxycarbamoyl)-2-propylthio]butylyl]-N,O-dimethyltyrosine amide, a pharmaceutically acceptable salt thereof or a stereoisomer thereof.

7. A pharmaceutical composition which comprises the compound (I) of claim 1, a pharmaceutically acceptable salt thereof, a pharmaceutically acceptable hydrate thereof, a pharmaceutically acceptable solvate thereof or a stereoisomer thereof and a pharmaceutically acceptable carrier.

* * * * *

UNITED STATES PATENT AND TRADEMARK OFFICE
CERTIFICATE OF CORRECTION

PATENT NO. : 5,442,110

DATED : August 15, 1995

INVENTOR(S) : Isomura, et al

It is certified that error appears in the above-identified patent and that said Letters Patent is hereby corrected as shown below:

On title page,

Item [22], change "Nov. 2, 1994" to --Nov. 2, 1992--.

Signed and Sealed this

Seventh Day of November, 1995

*Attest:*

BRUCE LEHMAN

*Attesting Officer*     *Commissioner of Patents and Trademarks*